Figure 1A:
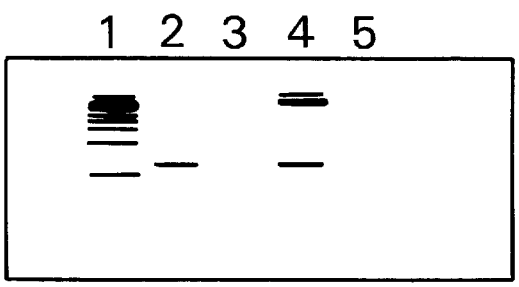

United States Patent

Breivik et al.

[11] Patent Number: 6,090,935
[45] Date of Patent: Jul. 18, 2000

[54] ISOLATION OF NUCLEIC ACID

[75] Inventors: Jarle Breivik; Gustav Gaudernack; Anne Spurkland, all of Oslo, Norway

[73] Assignee: Medinnova SF, Oslo, Norway

[21] Appl. No.: 08/640,891

[22] PCT Filed: Nov. 10, 1994

[86] PCT No.: PCT/GB94/02469

§ 371 Date: Oct. 28, 1996

§ 102(e) Date: Oct. 28, 1996

[87] PCT Pub. No.: WO95/13368

PCT Pub. Date: May 18, 1995

[30]     Foreign Application Priority Data

Nov. 11, 1993 [GB] United Kingdom ................... 9323305

[51] Int. Cl.[7] .............................. C07H 21/00; C12Q 1/68; G01N 33/553; G01N 33/546
[52] U.S. Cl. .................... 536/25.4; 536/22.1; 536/25.41; 536/25.42; 435/6; 435/91.2; 435/91.1; 436/533; 436/63; 436/174; 436/403; 436/526; 436/532
[58] Field of Search ............................. 435/91.2, 6, 91.1, 435/526, 532, 533, 63, 174, 403; 536/25.4, 22.1, 25.41, 25.42

[56]            References Cited

U.S. PATENT DOCUMENTS

| 4,336,173 | 6/1982 | Ugelstad ................................. 523/205 |
| 5,200,314 | 4/1993 | Urdea ......................................... 435/6 |
| 5,646,001 | 7/1997 | Terstappen et al. .................... 435/7.21 |

FOREIGN PATENT DOCUMENTS

| 0 393 744 A1 | 9/1989 | European Pat. Off. ........ C12P 19/34 |
| 0 389 063    | 9/1990 | European Pat. Off. .                    |
| 0 393 744    | 10/1990| European Pat. Off. .                    |
| WO 83/03920  | 11/1983| WIPO .                                   |
| WO 92/08133  | 5/1992 | WIPO .                                   |

OTHER PUBLICATIONS

Chen and Viola, A Method to Detect ras Point Mutations in Small Subpopulations of Cells, Analytical Biochemistry 195:51–56, 1991.

Haliassos et al., Modification of Enzymatically Amplified DNA for the Detection of Point Mutations, Nucleic Acid Research 17:3606, 1989.

Kahn et al., Rapid and Sensitive Nonradioactive Detection of Mutant K–ras Genes Via 'Enriched' PCR Amplification, Oncogene 6:1079–1083, 1991.

Kahn et al., Rapid Nonradioactive Detection of ras Oncogenes in Human Tumors, Amplifictions 4:22–26, 1990.

Kumar and Barbacis, Oncogene Detection at the Single Cell Level, Oncogene 3:647–651, 1988.

Wahlberg et al., Rapid Detection and Sequencing of Specific in vitro Amplified DNA Sequences Using Solid Phase Methods, Molecular and Cellular Probes 4:285–297, 1990.

Technical Handbook, Molecular Biology, Dynal, pp. 1–48, 1992.

*Primary Examiner*—Jezia Riley
*Attorney, Agent, or Firm*—Fish & Richardson P.C.

[57]            ABSTRACT

The invention provides a method for isolating nucleic acid from a sample, said method comprising boiling said sample and allowing it to cool, and condensing the nucleic acid onto a high-surface area solid support, and in particular the use of such a method in the preparation of nucleic acid samples for subsequent amplification. The method has particular utility in the isolation of nucleic acid from aged, fixed or otherwise distressed samples.

24 Claims, 1 Drawing Sheet

ISOLATION OF NUCLEIC ACID

The present invention relates to the isolation of nucleic acid, especially DNA, and in particular to a method for preparing nucleic acid samples for subsequent use in amplification procedures.

Techniques for the amplification of nucleic acids have recently revolutionised molecular biology and are now established as an indispensable tool in many procedures, for example in the detection and diagnosis of genetic and infectious diseases, in forensic medicine, in the identification of new genes or allelic variations or mutations, and in aiding routine genetic manipulations e.g. sequencing.

However, whilst new and improved amplification procedures are continually being developed, there are in certain cases particular drawbacks which limit the utility of the technique. Thus for example, DNA-based diagnostic techniques relying on DNA amplification, e.g. by the polymerise chain reaction (PCR), to detect the presence of microbial genes have proved useful in detecting bacterial and viral infectious agents and pathogenes and are rapidly acquiring importance. Nevertheless, in view of certain problems the techniques are not suitable for all diagnostic uses. One major problem is that amplification techniques such as PCR cannot be used directly on clinical samples, notably faeces or blood, which contain substances which inhibit the amplification enzymes, e.g. polymerases. The presence of red blood cells or haemoglobin presents a particular problem, and these generally need to be removed. A similar problem applies in the case of detecting microbial contamination in food samples, which also often contain inhibitory substances.

For successful amplification, the sample either has to be diluted very many times or the DNA has to be isolated and purified from the sample. In the former case, dilution to a degree sufficient to permit amplification frequently entails an unacceptable loss of sensitivity. In the latter case, nucleic acid purification techniques, involving for example extraction with phenols, chloroform and alcohols are often tedious, complicated and time consuming and may lead to loss of sample DNA, which can be a problem if the sample is small.

PCR has also proved difficult to apply to samples which are old, which have been chemically treated (for example by fixing or embedding) or which are otherwise distressed. This significantly impairs the utility of the technique in for example the analysis of fixed archival material or of blood and tissue samples which are not fresh or which have not been stored under refrigeration. Fixation techniques now generally used do not permit ready release of DNA suitable for the subsequent amplification using conventional techniques, and whilst improved, less damaging, fixation techniques are being developed, the situation is not entirely satisfactory. Complicated treatment procedures, e.g. deparaffinization of paraffin-embedded material, proteinase digestion etc are generally required and in many cases amplification cannot be achieved at all. This applies also in the case of aged or non-refrigerated samples.

There therefore exists a need for an improved method for preparing nucleic acid for use in amplification procedures, which is quick and simple to perform and which may be used on aged, non-refrigerated, fixed or otherwise treated or distressed samples. The present invention addresses this need.

We have now found that nucleic acid may be isolated from a sample in a form directly suitable for amplification by a simple and easy to perform procedure which involves boiling or heating the sample to a high temperature and allowing it to cool, and depositing the nucleic acid onto a solid support. This procedure avoids many of the complicated and time-consuming treatment steps of the prior art and, more importantly, can successfully be directly applied to clinical and other blood-containing samples and to samples which are aged, non-refrigerated or fixed, where previous techniques have proved unsuccessful. More particularly, the invention is based on the surprising discovery that when a sample is treated in this manner, nucleic acid released is able to condense around the support, thereby allowing it to be separated from the sample, whilst at the same time, retaining the ability to act as a template in a subsequent amplification reaction.

According to one aspect, the present invention thus provides a method for isolating nucleic acid from a sample, said method comprising boiling said sample and allowing it to cool, and condensing the nucleic acid onto a high-surface area solid support.

As mentioned above, this method has particular utility in the preparation of nucleic acid samples for amplification procedures since the resulting condensed nucleic acid samples can be used directly as the template for amplification without requiring prior removal from the support.

The nucleic acid may be DNA, RNA or any modification thereof. Preferably however the nucleic acid will be DNA, which may be genomic or cDNA, and single or double stranded. Where the method is used to prepare nucleic acid for amplification, it will preferably be double-stranded genomic DNA.

The sample may be any sample containing nucleic acid, but preferably will be a clinical sample such as a blood, blood-derived, faeces or tissue sample or a sample which is aged or treated. Treated samples include those which have been fixed, for example in formalin, acetone, alcohols, or any known or proprietary fixative e.g. Omnifix, or embedded, for example in paraffin wax or artificial or natural resins. Aged samples includes any sample which has not been freshly taken, or immediately refrigerated. Such aged or treated samples thus include any source of nucleic acid, plant or animal. In addition to archival material, which may be very many years old e.g. over one hundred years, or more preferably over 50 or 20 years old, such samples therefore include samples of any biological tissue or fluid (e.g. blood, plasma, serum, organ or other tissue biopsies) which have not immediately been refrigerated or processed, e.g. clinical samples taken in remote areas which need to be transported and/or stored sometimes over a period of days, weeks or months, before they can be processed or analyzed.

This represents an important advantage of the present invention, as in the past it has proved extremely difficult, if not impossible, to perform PCR or other amplifications on clinical samples, e.g. blood or biopsies which have had to be transported, for example by post, to a reference laboratory for analysis. Thus, advantageously, the present invention may be used when medical studies are conducted in remote regions of the world, where specialised equipment and personnel are lacking, and where samples require fixation and/or storage for extended periods of time before analysis. Particularly advantageously, the need for refrigeration may be avoided which is of significant benefit where samples need to be transported, e.g. by post, Other samples on which the invention has been shown to work successfully in preparing nucleic acid for amplification where previous methods have failed, include hair roots and cells of the cheeklining, obtained by mouthwashes, scrapings, etc. The method of the invention has been shown to work particularly favourably on samples which contain fragmented nucleic acid. "Boiling" as used herein, includes heating of the sample to high temperature, e.g. to at least 80° C., more preferably at least 85 or 90° C.

The duration and temperature used in the boiling step is to some extent dependant on the nature and state of the nucleic acid containing sample. Chemically treated, e.g. formalin treated, or aged samples generally require and can withstand more aggresive treatment than fresh cell suspensions. In general, the boiling stage will conveniently be effected for 10 seconds to 1 hour, or more if convenient, for example 30 seconds to 30 minutes, or more particularly 3 to 15 minutes. Thus, for example, for most samples treatment at 94° C. for 10 minutes will normally allow sufficient nucleic acid isolation to permit effective amplification.

The support may be present with the sample during the heat treatment or it may be introduced subsequently, even days or hours after the sample has been allowed to cool. For fresh cell suspensions it will generally be convenient to introduce the support before, during or shortly after the boiling stage; however for samples where quantities of detritus separate out as a result of the boiling stage it will generally be preferred to introduce the support after such detritus has been removed. Thus for samples such as paraffin-embedded tissue, boiling produces an inhomogeneous mixture containing tissue and wax fragments. It is preferred to separate off the nucleic acid containing liquid phase from these mixtures, e.g. by decanting or pipetting, after boiling and optionally after cooling and then to introduce that liquid phase to the support to allow the nucleic acid condensation to occur.

The nucleic acid condensation (and preferably also the boiling and cooling steps) in the method of the invention is preferably carried out in a high-salt aqueous solution (e.g. having an osmolality equivalent to that of at least 1 M NaCl aqueous solution).

Where condensation is effected by contacting the support with an already boiled and cooled nucleic acid containing aqueous sample, such contact is preferably made for a period of some minutes, e.g. 1 to 60, especially 10 to 20 minutes to allow the condensation, i.e. the binding of the nucleic acid to the support, to occur to an adequate extent.

The high-surface area support may be any known or conventional solid support presenting a high surface area for condensation of the nucleic acid. Such supports will generally have an irregular surface, and may for example be porous or particulate eg. particles, fibres, webs, sinters, or sieves. Condensation of the nucleic acid may take place on or around the support, or in it, if it has a porous structure for example. Examples of suitable solid supports include microtitre wells, capillaries, fibres, filters and dipsticks, although particulate supports are generally preferred, especially beads, as they, with their captured, "condensed" nucleic acid, may readily be used directly in a subsequent amplification step without any need to detach the condensed nucleic acid from the support.

Conveniently, a particulate solid support used according to the invention will comprise spherical beads. The size of the beads is not critical, but they may for example be of the order of diameter of at least 1 and preferably at least 2 $\mu$m, and have a maximum diameter of preferably not more than 10 and more preferably not more than 6 $\mu$m. Beads of diameter 2.8 $\mu$m and 4.8 $\mu$m have been shown to work well.

Monodisperse particles, that is those which are substantially uniform in size (e.g. size having a diameter standard deviation of less than 5% have the advantage that they provide very uniform reproducibility of reaction. Monodisperse polymer particles produced by the technique described in U.S. Pat. No. 4,336,173 are especially suitable.

Non-magnetic polymer beads suitable for use in the method of the invention are available from Dyno Particles AS (Lillestrøm, Norway) as well as from Qiagen, Pharmacia and Serotec.

However, magnetic particles are particularly preferred as a solid support according to the invention, as they lend a number of advantages, Most notably, magnetic aggregation provides a quick, simple and efficient way of separating the particles following the condensation step, and is a far less rigorous method than traditional techniques such as centrifugation which generate shear forces which degrade nucleic acids.

Magnetic particles suitable for use as supports in the method of the invention are available from Dynal, Advanced Magnetics Inc., Biotechnologies Ltd., Amersham, Promega, Scigen, Advanced Genetic Technologies and Seradyn.

Especially preferred are superparamagnetic particles, for example those described by Sintef in WO-A-83/03920, as magnetic aggregation and clumping of the particles during reaction can be avoided, thus ensuring uniform and nucleic acid abstraction.

The well-known magnetic particles sold by Dynal AS (Oslo, Norway) as DYNABEADS, are particularly suited to use in the present invention. Particular mention may be made of Dynabeads® M-450 and M-280.

It may be noted that the method of the invention works well despite previous studies using such magnetic particles having shown that non-specific binding of DNA and/or RNA to such surfaces is very low.

To improve the selectivity and performance of the technique, especially where only minute quantities of a sample are available, oligonucleotide probes specific for particular genes or nucleotide sequences may additionally be used, optionally together with stringent washing. Thus a specific probe may be introduced into the sample, binding to a specific target sequence. To facilitate isolation of the target nucleic acid from the sample, the solid support may be provided with means for capture of the probe. Generally, this will be accomplished by providing each of the probe and the support with one of a pair of corresponding affinity binding partners, such that the probe and the support may be bound together selectively, and if desired, reversibly. Most conveniently the affinity binding partner will comprise biotin and avidin/streptavidin, the biotin being bound to the probe and the avidin/streptavidin to the support. Both biotin-labelled oligonucleotide probes and streptavidin-coated magnetic particles are commercially available (Dynal AS).

Other binding partner systems may however be used, for example DNA-binding proteins binding to specific regions of the oligonucleotide probe e.g. the lac repressor protein Lac I binding to a lac operator (LacOP) site which may be provided on the probe. Alternatively, the oligonucleotide probe may be labelled with a hapten such as digoxigenin, and the support may be provided with an anti-hapten antibody. Techniques for labelling oligonucleotides with haptens such as digoxigenin are well known in the art as are methods for attachment of antibodies to solid supports.

Such a system is especially suited to the preparation of samples containing specific target nucleic acid sequences of interest, for amplification reactions. In particular we have shown that where prior art methods based upon isolation of target DNA for PCR by the use of specific biotin-labelled probes bound to streptavidin-coated magnetic beads have failed, e.g. in the case of blood containing samples, or aged or fixed samples, the method of the present invention has worked successfully.

According to a further aspect, the present invention thus provides a method of preparing a nucleic acid sample for in vitro amplification, said method comprising, sequentially or simultaneously, contacting said sample with an oligonucleotide probe specific for a target nucleotide sequence within said sample, and boiling said sample, subsequently allowing the sample to cool, and condensing the nucleic acid onto a high surface area solid support, wherein each of the oligonucleotide probe and solid support is provided with one of a pair of affinity binding partners, whereby the probe, and hence the target nucleotide sequence is bound to the support.

Alternatively viewed, this aspect of the invention provides a method of amplification of nucleic acid within a sample, said method comprising the steps of (a) sequentially or simultaneously, contacting said sample with an oligonucleotide probe specific for a target nucleotide sequence within said sample, and boiling said sample, subsequently allowing the sample to cool and condensing the nucleic acid onto a high surface area solid support, wherein each of the oligonucleotide probe and solid support is provided with one of a pair of affinity binding partners, whereby the probe, and hence the target nucleotide sequence is bound to the support, and (b) subjecting nucleic acid isolated by step (a) to an in vitro amplification reaction.

Conveniently, the sample may be allowed to cool in the presence of a solid support, whereby the nucleic acid condenses on or in the support.

Generally, as mentioned above the affinity binding partner pair will comprise biotin/streptavidin. This binding partner system is commonly used in molecular biology applications and many methods of incorporating or attaching biotin and streptavidin to the probe/support respectively, are known. Thus for example biotin may be incorporated by and streptavidin may be coated onto the support as discussed by Dynal AS in their "Technical handbook, molecular biology". The length of the oligonucleotide probe is not critical but may conveniently lie in the range of 10–200 nucleotides, more preferably 15–50 nucleotides.

In the case where the solid support is in the form of particles, the functionalisation of the particles and subsequent attachment of probes is conveniently such that each particle carries $10^3$–$10^6$ probes or probe binding sites.

A number of in vitro amplification techniques have been developed and may be used according to the present invention. PCR and its modifications, e.g. the use of nested primers, will however generally be the principal technique to be used.

In classical PCR, two primers are required and these may either be specific to a target DNA sequence of interest, or one or two standard PCR primers. This may necessitate introducing a hybridisation site for a standard PCR primer according to techniques well known in the art e.g. by restriction and ligation.

Nested PCR involves the use of two further so-called "inner" primers, which hybridise or "nest" between the first "outer" primer pair in a second series of amplification cycles. The use of four separate priming events results in increased specificity of the amplification reaction.

The nested primer technique has further been modified in the DIANA (Detection of Immobilised Amplified Nucleic Acids) system (see Wahlberg et al., Mol. Cell Probes 4:285 (1990)), in which the inner, second pair of primers carry, respectively, means for immobilisation to permit capture of amplified DNA, and a label or means for attachment of a label to permit recognition. This provides the dual advantages of a reduced background signal, and a rapid and easy means for detection of the amplified DNA.

Other amplification techniques worthy of mention include Self-sustained Sequence Replication (SSR), the Q-beta replicase amplification system and the Ligase Amplification Reaction (LAR).

In SSR, primers are used which carry polymerase binding sites permitting the action of reverse transcriptase to amplify target RNA or ssDNA.

In the Q-beta replicase system, an immobilized probe captures one strand of target DNA and is then caused to hybridise with an RNA probe which carries as a template region a tertiary structure known as MDV-1 for an RNA-directed RNA polymerase, normally Q-beta replicase.

LAR hybridises two oligonucleotide probes to adjacent positions on the target nucleic acid so that ligation, e.g. using T4 ligase, produces a longer sequence, which after strand separation, can function as a template for further hybridisations and ligations.

In the methods of the invention, the order in which the various steps are performed is not critical and variations and modification are possible. For example, the solid support may be added to the sample prior to boiling, or after the boiling step. The primers/probes required for amplification may likewise be added prior to the boiling step, immediately after boiling, or after the cooling condensation step.

The use of magnetic particles as solid supports particularly facilitates the washing and separation steps and has a significant advantage in that all the reactions, including amplification, may be performed in one reaction vessel, thereby considerably simplifying the reaction process and avoiding loss of nucleic acid fragments adhering to the vessel walls.

Boiling of the sample may take place in any known or conventional medium known in the art for manipulation of nucleic acids. Thus for example many typical buffers e.g. washing buffers, are known and can be used. Generally the use of high salt (e.g. 1–4M) aqueous media is preferred. Exemplary buffers include Tris-buffered saline solutions, and Dynal AS's Binding and Washing buffer (10 mM Tris-HCl, 1 mM EDTA, 2.0M NaCl, pH 7.5) is particularly suitable. Similar buffers may be used for any intermediate washing steps which may be required. It has been found favourable to include salt, e.g. 1 to 4 M NaCl, preferably 2M NaCl, in the boiling medium.

Incubation times for boiling may vary between 10 seconds and several hours, more conveniently between 1 and 15 minutes. Thus for example, favourable results have been achieved by heating samples to a temperature of 80 to 100° C. for a period of 10 minutes, or in some cases, 3 to 5 minutes.

Cooling may take place simply by allowing the sample to stand at ambient temperature, for example for a period of 3 to 20 minutes.

In the case where specific oligonucleotide probes are used, it may be possible to control to some degree the degree of nucleic acid fragmentation and the level of nucleic acid denaturization and condensation and hence the degree of specificity, by reducing the duration and/or temperature of the boiling step.

The methods of the invention has been found to work successfully with sample volumes of 0.1 µL to 100 mL. Generally small sample volumes of 1 to 100 µL, e.g. 10 to 20 µL are preferred. In the case where particles are used as solid support, amounts of 1 to 500 µg preferably 20 to 200 µg may conveniently be used.

The ability of the method of the invention to be performed with such small sample quantities is of particular benefit as the quantity of sample available is often very limited, e.g. with needle biopsy and forensic samples or where it is important to keep the sample for further study.

Where an oligonucleotide probe is used to enhance specificity, amounts of 0.1 pmol to 50 pmol, e.g. 1 to 5 pmol may be used.

The components required to perform the method of the invention may conveniently be supplied in the form of kits, and such kits form a further aspect of the invention. In a preferred embodiment such a kit would generally comprise the reagents needed to identify particular gene segments from any given sample type, and particular examples of such kits would be for selective amplification of ras or HLA genes or their mutations, e.g. K-ras and its 12/13 codon point mutations. Typically such kits will include magnetic beads for nucleic acid condensation; aqueous medium, e.g. buffered saline, for the heat treatment step; 5' and 3' end primers, nucleic acid polymerase and restriction enzymes for PCR amplification and, if desired RFLP assay; and, optionally, oligonucleotide probes conjugated or conjugable to the beads (e.g. biotinylated probes which are conjugable to streptavidin coated beads) which hybridize to some or all of the gene sequence or to adjacent sequences.

As mentioned above, the method of the invention has a number of uses and applications. These include for example the detection of pathogens, diseases and allelic variations. Clinical samples may be screened for epidemiological information. A major proposed use is in the analysis of clinical samples taken at remote locations which are transported to reference laboratories; blood samples may for example be directly posted without refrigeration once nucleic acid condensation and plasma and cell fragment purging has taken place. Thus the samples may be treated on site by the simple boiling step to condense the nucleic acid on to a solid support prior to flushing off sample other remnants and subsequent transport.

The technique also has utility in forensic medicine, and in all disciplines where sample or specimen storage is required e.g. in zoology, botany, conservation and evolutionary biology, the study of biological diversity or ecological processes.

Figure 1B:
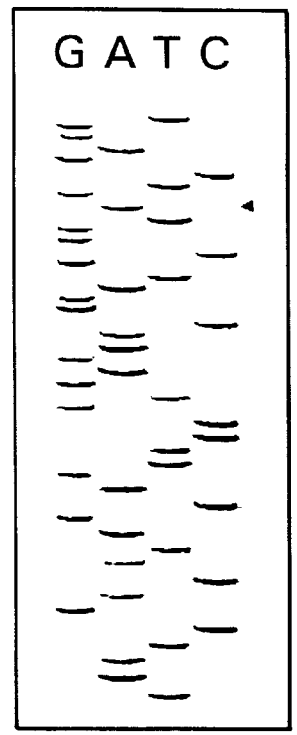
Figure 2A:
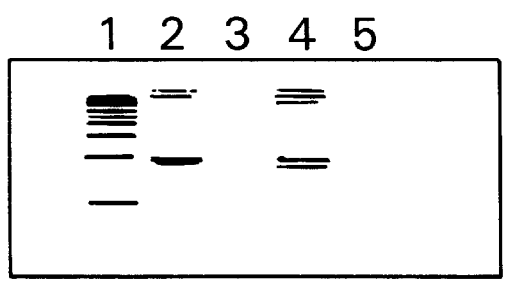
Figure 2B:
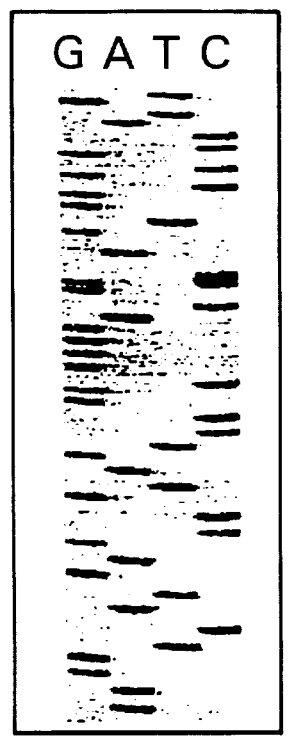

The invention will now be described by the following non-limiting Examples, with reference to the drawings in which:

FIGS. 1a and 1b show
(a) the results of gel electrophoresis following restriction fragment length polymorphism (RFLP) analysis of the PCR products of Example 1:
Lane 1: Marker DNA.
Lane 2: PCR from magnetic isolated DNA from small amount of fixed tumour tissue.
Lane 3: PCR from 5 µl of liquid from boiled sample
Lane 4: PCR from 1 µg of mutated control DNA (positive control).
Lane 5: PCR without DNA (negative control);
(b) gel electrophoresis showing the results of solid phase sequencing of the mutated PCR product (ras gene mutation) (Lane 2 of FIG. 1(a)) mutation indicated by arrow;

FIGS. 2a and 2b show
(a) the results of gel electrophoresis following restriction fragment length polymorphism (RFLP) analysis of the PCR products of Example 2:
Lane 1: Marker DNA.
Lane 2: PCR from magnetic isolated DNA from blood sample.
Lane 3: PCR from 5 µl of liquid from boiled sample.
Lane 4: PCR from 1 µg of control DNA (positive control).
Lane 5: PCR without DNA (negative control);
(b) gel electrophoresis showing the results of solid phase sequencing of the mutated PCR product (HLA-DQB gene sequence) (Lane 2 of FIG. 2(a)).

EXAMPLE 1

Identification of K-ras mutation from pancreatic cancer

Two 5 µm thick slides are cut from the paraffin block from a formalin-fixed paraffin-embedded needle-biopsy from a pancreatic cancer and added to 400 µL of Binding & Washing buffer (10 mM Tris-HCl, pH 7.5, 1 mM EDTA, 2.0 M NaCl) containing 3 pmol of a biotinylated oligonucleotide (e.g. 5'-B-ACTGA ATATA AACTT GTGGT AGTTG GACCT-3') complimentary to the 5'-end of the K-ras gene segment.

The tubes are incubated at 94° C. for 5 minutes and the contents mixed twice on a vortex-mixer for 20 seconds during this incubation.

When the tubes have been cooled to ambient temperature in a thermal cycler for about 3 minutes, the liquid phase is pipettes off and mixed with 20 µg of streptavidin coated paramagnetic beads (Dynabeads® M-280 streptavidin, Dynal, Norway).

The mixture is left at ambient temperature for 15 minutes.

The beads are isolated by magnetic separation (Dynal MPC®-E, Dynal, Norway), and added as template to a K-ras specific PCR reaction-mix (e.g. using the 5' and 3' end primers 5'-ACTGA ATATA AACTT GTGGT AGTTG GACCT-3' and 5'-TCAAA GAATG GTCCT GGAAC-3', and Taq DNA polymerase) 5 µL of the boiled liquid, collected before the beads are added, is used as template in a parallel control procedure.

Three serial PCR's with two intermediate destructions of non-mutated alleles by-a specific endonuclease (e.g. Bst NI) are performed.

For RFLP analysis the amplification products are digested, e.g. with Bst NI and analysed using gel electrophoresis, Results are shown in FIG. 1a. A detectable amplification product (lane 2) is obtained from the PCR where beads carrying DNA served as template, but not when the bead free boiled liquid is used (lane 3).

The PCR-product is identified as mutated by RFLP, and the nucleotide sequence was determined by solid-phase sequencing (FIG. 1b) indicating the presence of a point mutation in codon 12.

Conventional PCR amplification of and RFLP assays for ras oncogenes have been discussed in several publications and the primers and enzymes conventionally used may be used in the method of the invention. Such publications include Kahn et al. Amplifications 4:22–26 (1990), Chen et al. Anal. Biochem. 195:51–56 (1991), Kahn et al. Oncogene 6:1079–1083 (1991), Haliassos et al. Nucleic Acids Research 17:3606 (1989) and Kumar et al. Oncogene 3:647–651 (1988).

EXAMPLE 2

HLA-typing of an old blood sample

10 µl of EDTA-blood, stored at ambient temperature for 7 days, was added to 200 µl of Binding & Washing buffer (10 mM Tris-HCl, pH 7.5,m 1 mM EDTA, 2.0 M NaCl) mixed with 20 µg of paramagnetic beads (Dynabeads® M-450, Dynal, Norway). A parallel control sample was prepared without beads.

The tubes were then incubated at 94° C. for 10 minutes and cooled to ambient temperature.

The beads were isolated by magnetic separation (Dynal MPC®-E, Dynal, Norway), and added to a HLA-DQB specific PCR reaction-mix (e.g. using the 5' and 3' end primers DQ-AMP A: 5'-GCATG TGCTA CTTCA CCAAC G-Biotin 3' and DQ-AMP B:5'-CAGGT AGTTG TGTCT GCACA C-3', and Taq DNA polymerase). 5 µl of the sample solution prepared without beads, was used as template in a parallel control procedure.

A 30 cycle PCR was performed.

For RFLP analysis the amplification products were analysed using gel electrophoresis. The results are shown in FIG. 2a.

A detectable amplification product (column 2) was obtained from the PCR where beads carrying DNA served as template, but not when the bead free boiled liquid was used (column 3).

The nucleotide sequence was determined by solid-phase sequencing (FIG. 2b).

General Method Steps

For use in nucleic acid fragment amplification, the method of the invention may thus conveniently be effected using the following steps:

Step 1:
Nucleic acid release from sample by boiling, in the presence (Example 2) or absence (Example 1) of solid support and in the presence (Example 1) or absence (Example 2) of an oligonucleotide probe.

Step 2:
Nucleic acid binding to solid support.
a) Cooling in the presence of solid support (Example 2).
b) Adding solid support to the cooled liquid (Example 1)

Step 3:
Isolation of solid support with bound nucleic acid (e.g. magnetic separation).

Step 4:
Solid support with bound nucleic acid used as template in a subsequent amplification reaction.

What is claimed is:

1. A method for isolating nucleic acid from a sample, said method comprising boiling said sample, cooling the boiled sample, allowing the nucleic acid in the liquid phase of the cooled sample to directly bind to a solid support comprising magnetic particles, and separating the solid support with the nucleic acid bound thereto from the remainder of said liquid phase.

2. A method as claimed in claim 1 wherein the nucleic acid is DNA.

3. A method as claimed in claim 1 wherein the sample is a clinical sample.

4. A method as claimed in claim 1, wherein the sample is fixed.

5. A method as claimed in claim 1, wherein the sample is aged.

6. A method as claimed in claim 1, wherein the boiling step is effected by heating the sample to at least 80° C.

7. A method as claimed in claim 6, wherein the sample is heated for 10 seconds to 1 hour.

8. A method as claimed in claim 1, wherein the support is added to the sample prior to or during the boiling step.

9. A method as claimed in claim 1, wherein the support is added to the sample after the boiling step.

10. A method as claimed in claim 1, wherein at least one of the boiling, cooling, and contacting steps is carried out in a high salt aqueous solution.

11. A method as claimed in claim 2, wherein the nucleic acid is genomic DNA.

12. A method as claimed in claim 3, wherein the nucleic acid is genomic DNA.

13. A method as claimed in claim 3, wherein the sample is a blood sample.

14. A method as claimed in claim 3, wherein the sample is a tissue sample.

15. A method as claimed in claim 13, wherein the nucleic acid is genomic DNA.

16. A method as claimed in claim 14, wherein the nucleic acid is genomic DNA.

17. A method for isolating nucleic acid from a sample that is fixed or aged, said method comprising boiling the fixed or aged sample, cooling the boiled sample allowing the nucleic acid in the cooled sample to directly bind to a solid support having a high surface area comprising magnetic particles, and separating the solid support with the nucleic acid bound thereto from the remainder of the cooled sample.

18. A method as claimed in claim 17 wherein the nucleic acid is DNA.

19. A method as claimed in claim 17, wherein the boiling step is effected by heating the sample to at least 80° C.

20. A method as claimed in claim 17, wherein the support is added to the sample prior to or during the boiling step.

21. A method as claimed in claim 17, wherein the support is added to the sample after the boiling step.

22. A method as claimed in claim 17, wherein at least one of the boiling, cooling and contacting steps is carried out in a high salt aqueous solution.

23. A method as claimed in claim 17, wherein the solid support is particulate.

24. A method as claimed in claim 18, wherein the nucleic acid is genomic DNA.

* * * * *